United States Patent [19]

Murray et al.

[11] Patent Number: 5,648,585
[45] Date of Patent: Jul. 15, 1997

[54] PROCESS FOR ISOMERIZING LINEAR OLEFINS TO ISOOLEFINS

[76] Inventors: Brendan Dermot Murray, 1118 Stoney Hill Dr., Houston, Tex. 77077; Bruce Herman Charles Winquist, 11202 Coldspring Dr., Houston, Tex. 77043; Donald Henry Powers, 6007 Silent Oaks Dr., Humble, Tex. 77346; Jon Barin Wise, 814 Hyacinth Pl., Missouri City, Tex. 77459; Richard Brian Halsey, 14445 Wallisville, Houston, Tex. 77049

[21] Appl. No.: 175,010

[22] Filed: Dec. 29, 1993

[51] Int. Cl.$^6$ .................... C07C 5/22; C07C 5/27
[52] U.S. Cl. ............ 585/671; 502/34; 502/38; 502/41
[58] Field of Search ............... 585/671; 502/34, 502/38, 41

[56] References Cited

U.S. PATENT DOCUMENTS

| | | | |
|---|---|---|---|
| 4,038,337 | 7/1977 | Manara et al. | 585/671 |
| 4,367,362 | 1/1983 | Franz et al. | 585/671 |
| 4,434,315 | 2/1984 | Juguin et al. | 585/671 |
| 4,503,282 | 3/1985 | Sikkenga . | |
| 4,689,312 | 8/1987 | Ngoc Le et al. | 502/38 |
| 4,719,189 | 1/1988 | Krishnamurthy | 502/38 |
| 4,795,623 | 1/1989 | Evans . | |
| 4,942,027 | 7/1990 | Evans . | |
| 5,057,635 | 10/1991 | Gajda | 585/671 |
| 5,221,776 | 6/1993 | Alexander . | |
| 5,393,717 | 2/1995 | Apelian . | |
| 5,489,726 | 2/1996 | Huss, Jr. et al. | 585/671 |

FOREIGN PATENT DOCUMENTS

| | | |
|---|---|---|
| 0042252 | 6/1981 | European Pat. Off. . |
| 0501577A1 | 2/1992 | European Pat. Off. . |
| 0523838A2 | 6/1992 | European Pat. Off. . |
| 0545179A1 | 11/1992 | European Pat. Off. . |

*Primary Examiner*—Glenn A. Caldarola
*Assistant Examiner*—Elizabeth D. Wood

[57] ABSTRACT

This invention relates to a process in which a linear olefin is converted under isomerizing conditions to its corresponding methyl branched isoolefin by contact at a temperature of from 200° C. to 650° C. with an isomerizing catalyst comprising (i) at least one zeolite having only in one dimension a pore structure having a pore size small enough to retard by-product dimerization and coke formation and large enough to permit entry of the linear olefin and allow formation of the methyl branched isoolefin, (ii) an alumina binder and (iii) up to about 15% by weight of coke oxidation-promoting metal. After a period of operation, when sufficient coke has deposited on the catalyst in an amount to significantly reduce the activity of the catalyst, the catalyst is stripped of hydrocarbon and then contacted at elevated temperature with an oxygen-containing gas for a sufficient time to burn off the coke, i.e., to regenerate the catalyst at a temperature of less than about 565° C. After regeneration, the isomerization process is continued. The use of palladium and/or platinum as the coke oxidation-promoting metal is particularly desirable.

27 Claims, 1 Drawing Sheet

PROCESS FOR ISOMERIZING LINEAR OLEFINS TO ISOOLEFINS

FIELD OF THE INVENTION

This invention relates to a process for converting under isomerization conditions linear olefins to their corresponding methyl branched isoolefins. In a specific aspect, the invention relates to a process to prepare improved olefin isomerization catalysts and a process to regenerate these catalysts as to maintain high catalytic performance.

BACKGROUND OF THE INVENTION

Increasing demand for high octane gasoline blended with lower aliphatic alkyl ethers such as octane boosters and supplementary fuels has created a significant demand for isoalkylethers, especially the $C_5$ to $C_7$ methyl, ethyl and isopropyl-t-alkyl ethers, such as methyl t-butyl ether, ethyl t-butyl ether, t-amyl methyl ether and t-amyl ethyl ether. Consequently, there is an increasing demand for the corresponding isoalkene starting materials such as isobutene, isoamylenes and isohexenes.

To obtain isoolefins, it is desirable to convert an alkene such as normal butene, to a methyl branched alkene, for example isobutylene, by mechanisms such as structural isomerization. Such converted isoalkenes then can be reacted further, such as by polymerization, etherification or oxidation, to form useful products. Normal alkenes containing four carbon atoms (1-butene, trans-2-butene and cis-2-butene) and five carbon atoms (1-pentene, trans-2-pentene, and cis-2-pentene) are relatively inexpensive starting compounds. Conventionally, butenes and amylenes, including to a minor extent isobutylene and isoamylene, are obtained as a by-product from refinery and petrochemical processes such as catalytic and thermal cracking units. Butenes are also conveniently obtained from butadiene via selective hydrogenation.

Zeolite materials, both natural and synthetic, are known to have catalytic properties for many hydrocarbon processes. Zeolites typically are ordered porous crystalline aluminosilicates having a definite structure with cavities interconnected by channels. The cavities and channels throughout the crystalline material generally can be of such a size to allow selective separation of hydrocarbons. Such a hydrocarbon separation by the crystalline aluminosilicates essentially depends on discrimination between molecular dimensions. Consequently, these materials in many instances are known in the art as "molecular sieves" and are used, in addition to catalytic properties, for certain selective adsorptive processes. Zeolite molecular sieves are discussed in great detail in D. W. Breck, *Zeolite Molecular Sieves*, Robert E. Krieger Publishing Company, Malabar, Fla. (1984).

Generally, the term "zeolite" includes a wide variety of both natural and synthetic positive ion-containing crystalline aluminosilicate materials, including molecular sieves. They generally are characterized as crystalline aluminosilicates which comprise networks of $SiO_4$ and $AlO_4$ tetrahedra in which silicon and aluminum atoms are cross-linked in a three-dimensional framework by sharing of oxygen atoms. This framework structure contains channels or interconnected voids that are occupied by cations, such as sodium, potassium, ammonium, hydrogen, magnesium, calcium, and water molecules. The water may be removed reversibly, such as by heating, which leaves a crystalline host structure available for catalytic activity. The term "zeolite" in this specification is not limited to crystalline aluminosilicates. The term as used herein also includes silicoaluminophosphates (SAPO), metal integrated aluminophosphates (MeAPO and ELAPO), metal integrated silicoaluminophosphates (MeAPSO and ELAPSO). The MeAPO, MeAPSO, ELAPO, and ELAPSO families have additional elements included in their framework. For example, Me represents the elements Co, Fe, Mg, Mn, or Zn, and El represents the elements Li, Be, Ga, Ge, As, or Ti. An alternative definition would be "zeolitic type molecular sieve" to encompass the materials useful for this invention.

Developments in the art have resulted in formation of many synthetic zeolitic crystalline materials. Crystalline aluminosilicates are the most prevalent and, as described in the patent literature and in the published journals, are designated by letters or other convenient symbols. Various zeolites which have been specifically named and described are, for example, Zeolite A (U.S. Pat. No. 2,882,243), Zeolite X (U.S. Pat. No. 2,882,244), Zeolite Y (U.S. Pat. No. 3,130,007), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite ZSM-23 (U.S. Pat. No. 4,076,842), Zeolite ZSM-35 (U.S. Pat. Nos. 4,016,245 and 5,190,736), Zeolite ZSM-48 (U.S. Pat. No. 4,375,573), Zeolite NU-1 (U.S. Pat. No. 4,060,590) and others. Various ferrierite zeolites including the hydrogen form of ferrierite, are described in U.S. Pat. Nos. 3,933,974, 4,000,248 and 4,942,027 and patents cited therein. SAPO-type catalysts are described in U.S. Pat. No. 4,440,871. MeAPO type catalysts are described in U.S. Pat. Nos. 4,544,143 and 4,567,029; ELAPO catalysts are described in U.S. Pat. No. 4,500,651, and ELAPSO catalysts are described in European Patent Application 159,624.

Two general classes of catalysts have been disclosed as particularly useful for isomerizing a linear olefin to the corresponding methyl branched isoolefin. These include the porous, non-crystalline, refractory oxide-based catalysts and the zeolitic-based catalysts.

Examples of the porous non-crystalline, refractory oxide-based catalysts are aluminum oxides, such as gamma or eta $Al_2O_3$, halogenated aluminum oxides, aluminum oxides reacted with silicon, boron or zirconium, various phosphates and solid phosphoric acids. Examples of these catalysts are described in U.S. Pat. Nos. 5,043,523, 3,531,542, 3,381,052, 3,444,096, 4,038,337, 3,663,453, British Patent No. 2,060, 424 and in an article by V. R. Choudhary and L. K. Doraiswamy, "Isomerization of n-Butene to Isobutene, I. Selection of Catalyst by Group Screening," Journal of Catalysis, volume 23, pages 54–60, 1971. Illustrative of the porous, non-crystalline refractory oxide catalysts are those described in U.S. Pat. No. 4,434,315, issued Feb. 28, 1984, which discloses as a catalyst a porous alumina acidified with a critical amount of silica and containing 5 ppm to 2% by weight of palladium, chromium, nickel, copper, manganese or silver by impregnation. The use of the listed metals is said to result in a more facile catalyst regeneration. All of these catalysts deactivate rapidly. According to the examples in British Patent No., 2,060,424, run life can be as short as 1 to 2 hours. Often, it is necessary to add steam and halogen compounds to prolong the catalysts run life. German Specification No. 3,000,650-A states that the run life can be increased to approximately 50 hours by these methods although this is still less than desirable.

With regard to the zeolitic-based catalysts, the most significant use has involved the large pore zeolites or those having two or more-dimensional interconnecting channels. Examples of the zeolitic-based catalysts having two or more-dimensional interconnecting channels used in association with catalytic metals are U.S. Pat. No. 4,435,311 (with platinum and palladium) and U.S. Pat. Nos. 4,503,282 and 5,227,569 (impregnated or ion-exchanged with metals including Group VIII). Examples of the large pore zeolitic-based catalysts used in association with catalytic metals are U.S. Pat. No. 5,227,569 (impregnated or ion-exchanged with metals including Group VIII) and U.S. Pat. No. 4,392,003 (with gallium).

More recently, European Patent Publication Number 523, 838 A2, published Jan. 20, 1993, has disclosed a process for structurally isomerizing a linear olefin to its corresponding methyl branched isoolefin using as a catalyst a zeolite with one or more one-dimensional pore structure having a pore size small enough to retard by-product dimerization and coke formation within the pore structure. and large enough to permit entry of the linear olefin and allow formation of the methyl branched isoolefin. It has been found that as these small pore catalysts are used, they acquire a build-up of coke which diminishes their effectiveness. To restore their effectiveness, the catalysts must be regenerated at elevated temperatures by contact with oxygen. This regeneration process, when repeated a number of times, can have an adverse effect on the catalyst life and selectivity.

A typical zeolitic catalyst regeneration temperature is described in "Chemistry Of Catalytic Processes", by B. C. Gates, J. R. Katzer and G. C. A. Schuit, McGraw-Hill Book Company, New York (1979) at pages 1–5 as between a temperature of 650° C. to 760° C. A recent trend is toward higher regeneration temperatures. For example, a regeneration temperature as high as 850° C. is used in the commercial regeneration of zeolitic catalysts used in Fluid Catalytic Cracking ("FCC"). J. Biswas and I. E. Maxwell, *Applied Catalysis*, 63 (1990), 197–258.

However, it has been found that use of such high regeneration temperatures such as those used in FCC results in poor olefin isomerization performance (lower selectivity) for a medium pore-sized zeolite-based catalyst such as those described in European Patent Publication Number 523,838. According to U.S. Pat. No. 5,043,523, a regeneration temperature of 550° C. to 600° C. is recommended for a modified alumina catalyst of the type discussed earlier. The modified alumina catalyst was reported to show no signs of deactivation after undergoing 10 regeneration cycles at 575° C. by method A of Example 29. However, it has been found that zeolitic catalysts with one or more one-dimensional pore structure having a pore size small enough to retard by-product dimerization and coke formation within the pore structure and large enough to permit entry of the linear olefin and allow formation of the methyl branched isoolefin, such as ferrierite, ZSM-22 and ZSM-23 tend to lose selectivity for the formation of isoolefins when exposed to temperatures of greater than 565° C. for a period of time such as those used in the regeneration processes mentioned above.

Commercialization of an isomerization process to manufacture isoolefins from linear olefins has been further hampered by longer regeneration times compared with run life.

It is therefore an object of the present invention to provide a medium pore zeolite catalyzed process for structurally isomerizing a linear olefin to its corresponding methyl branched isoolefin with improved run life and/or reduced regeneration time. It is another object of the present invention to provide a medium pore zeolite catalyzed process for structurally isomerizing a linear olefin to its corresponding methyl branched isoolefin with improved overall yield. It is further an object of the present invention to provide an improved medium pore zeolite catalyst for structurally isomerizing a linear olefin to its corresponding methyl branched isoolefin.

SUMMARY OF THE INVENTION

In the process of this invention one or more linear olefins is converted under isomerizing conditions to its corresponding methyl branched isoolefins by contact at a temperature of from 200° C. to 600° C. with an isomerizing catalyst comprising (i) at least one zeolite having only in one dimension a pore structure having a pore size small enough to retard by-product dimerization and coke formation and large enough to permit entry of the linear olefin and allow formation of the methyl branched isoolefin, (ii) a binder and (iii) up to 15% by weight of coke oxidation-promoting metal. After a period of operation, when sufficient coke has deposited on the catalyst in an amount to reduce the activity and/or selectivity of the catalyst, the catalyst is separated from the olefin feed and contacted at a temperature of less than 565° C. with an oxygen-containing gas for a sufficient time to substantially burn off the coke, i.e., to regenerate the catalyst. After regeneration, the isomerization process is continued.

Enhanced catalyst operating performance is obtained when the catalyst is prepared by mulling together a zeolite powder, alumina powder, water, peptizing amount of acid and a compound of the coke oxidation-promoting metal, forming the mixture into a pellet, and calcining the pellet at a temperature of from 300° C. to 700° C.

The use of palladium and/or platinum as the coke oxidation-promoting metal is particularly desirable.

DETAILED DESCRIPTION OF THE PREFERRED EMBODIMENTS

Figure 1:
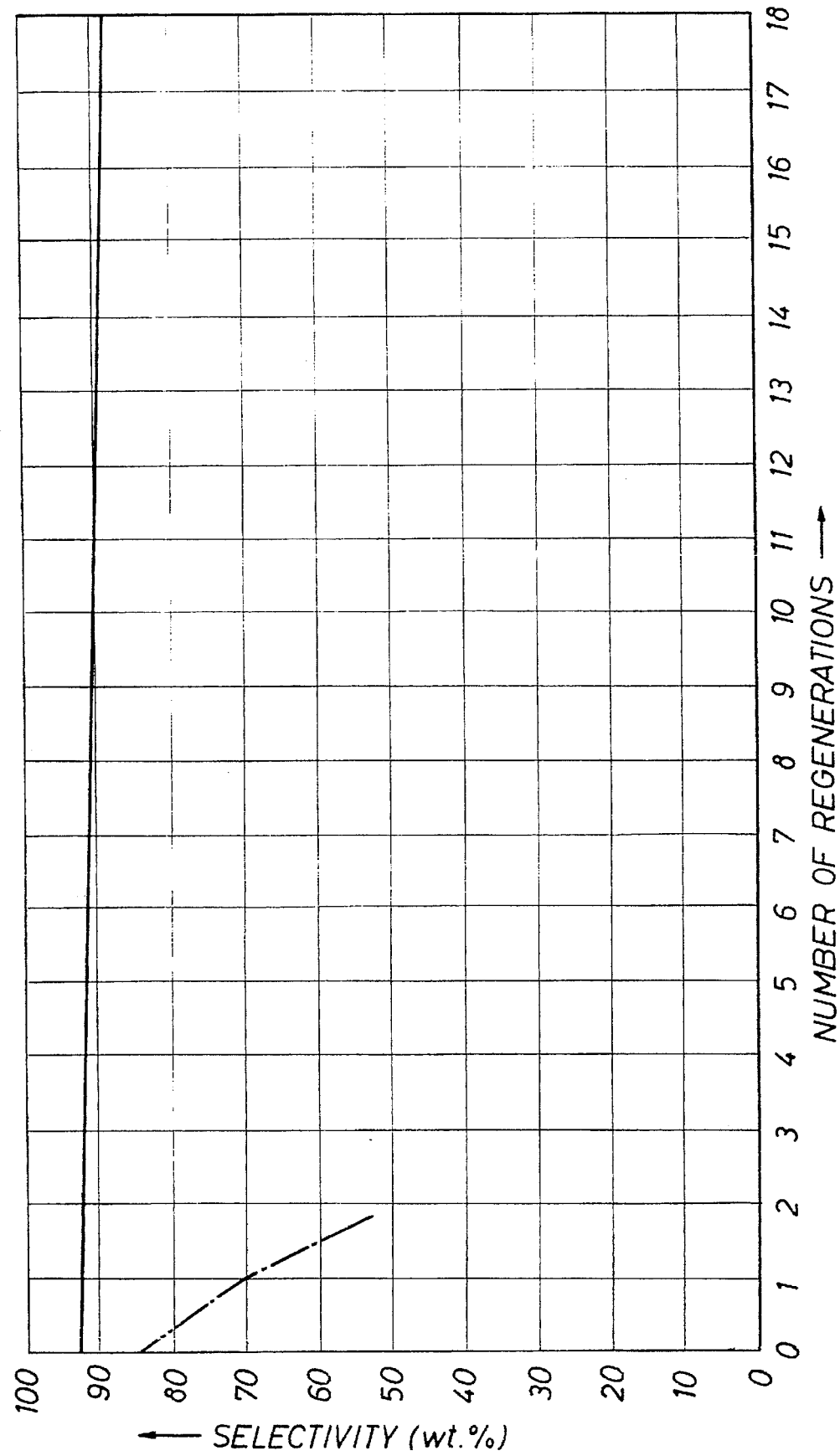
FIG. 1 is a plot of the selectivity to isobutylene obtained over a number of regenerations with Catalysts A (no palladium) and B (with palladium).

It has been found that a process for structurally isomerizing a linear olefin to its corresponding methyl branched isoolefin with run life longer than the regeneration time can be obtained by incorporating into the catalysts certain coke oxidation-promoting metals in an effective amount to promote burning off coke from the catalyst and carrying out the regeneration at a temperature of less than about 565° C. until the coke is substantially burned off. By incorporating the coke-oxidation-promoting metals and use of specific oxygen partial pressures, it has been found that the regeneration of the medium pore zeolites can be effected at lower temperatures which does not substantially negatively effect the performance of the catalyst. In addition, it has been found that by preparing the catalyst by consolidating and calcining a mulled zeolite powder, alumina powder, water, peptizing agent and coke oxidation-promoting metal provides an olefin isomerization catalyst with enhanced performance.

Isomerization Catalysts

The isomerizing catalysts used in the instant process comprise a zeolite as hereinafter defined, a binder and a coke-oxidation promoting metal.

The zeolite used in the isomerization catalyst of this invention comprises a zeolite having one-dimensional pore structures with a pore size ranging from greater than about 0.42 nm and less than about 0.7 nm. Zeolites with this specified pore size are typically referred to as medium or intermediate pore zeolites and typically have a 10-member (or puckered 12-member) ring channel structure in one dimension and an 9-member or less (small pore) in the other dimensions, if any. For purposes of this invention, a one-dimensional pore structure is considered one in which the channels having the desired pore size do not interconnect with other channels of similar or larger dimensions; it may also be considered alternatively as a channel pore structure (see U.S. Pat. No. 3,864,283) or uni-directional sieve.

The zeolite catalyst preferably comprises substantially only zeolites with the specified pore size in one dimension. Zeolites having pore sizes greater than 0.7 nm are susceptible to unwanted aromatization, oligomerization, alkylation, coking and by-product formation. Further, two or three-dimensional zeolites having a pore size greater than 0.42 nm in two or more dimensions permit dimerization and trimerization of the alkene. Hence, zeolites having a pore diameter bigger than about 0.7 nm in any dimension or having a two or three-dimensional pore structure in which any two of the dimensions has a pore size greater than about 0.42 nm are excluded as part of this invention. Zeolites that contain only small pores (i.e., less than about 0.42 nm) do not allow for diffusion of the methyl branched isoolefin product.

Examples of zeolites that can be used in the processes of this invention, which have one-dimensional pore structures with a pore size between about 0.42 nm and 0.7 nm, include the hydrogen form of ferrierite, ALPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, and MeAPSO-41, MeAPSO-46, ELAPO-11, ELAPO-31, ELAPO-41, ELAPSO-11, ELAPSO-31, and ELAPSO-41, laumontite, cancrinite, offretite, hydrogen form of stilbite, the magnesium or calcium form of mordenite and partheite. The isotypic structures of these frameworks, known under other names, are considered to be equivalent. An overview describing the framework compositions of many of these zeolites is provided in *New Developments in Zeolite Science Technology*, "Aluminophosphate Molecular Sieves and the Periodic Table," Flanigen et al. (Kodansha Ltd., Tokyo, Japan 1986).

Many natural zeolites such as ferrierite, heulandite and stilbite feature a one-dimensional pore structure with a pore size at or slightly less than about 0.42 nm diameter. These same zeolites can be converted to zeolites with the desired larger pore sizes by removing the associated alkali metal or alkaline earth metal by methods known in the art, such as ammonium ion exchange, optionally followed by calcination, to yield the zeolite in its hydrogen form. See e.g., U.S. Pat. Nos. 4,795,623 and 4,942,027 incorporated herein by reference. Replacing the associated alkali or alkaline earth metal with the hydrogen form correspondingly enlarges the pore diameter. It is understood that the pore diameter or "size" shall mean the effective pore diameter or size for diffusion. Alternatively, natural zeolites with too large a pore size, such as mordenite, can be altered by substituting the alkali metal with larger ions, such as larger alkaline earth metals to reduce the pore size and thus become useful for the processes of this invention.

Particularly preferred zeolites are those having the ferrierite isotypic framework structure (or homeotypic). See the *Atlas of Zeolite Structure Types*, by W. M. Meier and D. H. Olson, published by Butterworth-Heinemann, third revised edition, 1992, page 98. The prominent structural features of ferrierite found by x-ray crystallography are parallel channels in the alumino-silicate framework which are roughly elliptical in cross-section. Examples of such zeolites having the ferrierite isotypic framework structure include natural and synthetic ferrierite (can be orthorhombic or monoclinic), Sr-D, FU-9 (EP B-55,529), ISI-6 (U.S. Pat. No. 4,578,259), NU-23 (E.P. A-103,981), ZSM-35 (U.S. Pat. No. 4,016,245) and ZSM-38 (U.S. Pat. No. 4,375,573). ZSM-22 and ZSM-23 are also useful zeolites for preparing the catalysts of this invention. Hydrogen form of ferrierite (H-ferrierite) is the most preferred zeolite and considered to be comprised substantially of a one-dimensional structure having an elliptical pore size (>0.54 nm and >0.42 nm) large enough to permit entry of the linear olefin and diffusion of the methyl branched isoolefin and small enough to retard coke formation. Methods for preparing various H-ferrierite are described in U.S. Pat. Nos. 4,251,499, 4,795,623 and 4,942,027.

Exemplary of zeolites that are not useful for the processes of this invention include ZSM-5, ZSM-20, erionite, Beta, zeolite Y, hydrogen form of mordenite, and faujasite.

The zeolite catalyst used in the isomerization processes of this invention are combined with a refractory oxide that serves as a binder material. Suitable refractory oxides include natural clays, such as bentonite, montmorillonite, attapulgite, and kaolin; alumina; silica; silica-alumina; hydrated alumina; titania; zirconia and mixtures thereof. The weight ratio of zeolite and binder material suitably ranges from about 60:40 to about 99.5:0.5, preferably from about 75:25 to about 99:1, more preferably from about 80:20 to about 98:2 and most preferably from about 85:15 to about 95:5, measured as the oxide in the final catalyst. Preferably the binder is an alumina.

Binders useful in preparing the catalysts are any of the conventional alumina-containing binders known in the art for preparing catalysts and include, for example, the aluminas, the silica-aluminas and the clays. For purpose of the invention, alumina-containing binders include any of the alumina precursors including the hydrated forms of alumina such as bayerite, boehmite and gibbsite which upon calcination are converted to alumina ($Al_2O_3$). Preferred silica-aluminas are the amorphous silica-aluminas such as the aluminosilicate gels and sols. Non-limiting examples of the clays include bentonite, hectorite, kaolin, attapulgite and the like. The binders are provided in any convenient form, such as powders, slurries, gels or sols. When the binders are provided as slurries, gels or sols, at least part of the water used in the mulling step will be found as part of the slurry, gel or sol.

Preferred binders are aluminas, such as pseudoboehmite, gamma and bayerite aluminas. These alumina binders are readily available commercially and are used to manufacture alumina-based catalysts. LaRoche Chemicals, through its VERSAL® family of aluminas and Vista Chemical Company, through its CATAPAL® aluminas, provide suitable alumina powders which can be used as binders in preparing the instant catalysts. Preferred alumina binders to be used in the preparation of the catalyst, particularly when extrusion is utilized, are the high-dispersity alumina powders. Such high dispersity aluminas have a dispersity of greater than 50% in a aqueous acid dispersion having an acid content of 0.4 milligram equivalents of acid (acetic) per gram of $Al_2O_3$. Such high dispersity aluminas are exemplified by Vista's CATAPAL® D alumina.

The metals incorporated into the instant catalysts are metals that promote the oxidation of coke in the presence of oxygen at a temperature greater than about 250° C. While the term "metal(s)" is used herein in reference to the oxidation catalysts, it will be understood by one skilled in the art that these metals will not necessarily be in the zero-valent oxidation state and in many cases will be in the higher oxidation states. Thus, "metal(s)" can encompass the oxides as well as the metals.

Preferably the coke oxidation-promoting metal(s) used in the instant catalyst are transition and rare earth metals. More preferably the coke oxidation-promoting metals are selected from Groups IB, VB, VIB, VIIB and VIII of the transition metal series of the Periodic Table (CAS version). Specifically preferred are Pd, Pt, Ni, Co, Mn, Ag and Cr. Most preferred are the noble metals such as palladium and/or platinum.

The amount of the coke oxidation-promoting metal(s) introduced varies up to about 15% by weight, preferably the lower range of from about 5 parts per million ("ppm") and the upper range of up to about 15% by weight, preferably up to about 10% by weight, more preferably up to about 5% by weight measured as the metal per total weight of the catalyst. When using noble metal such as platinum and/or palladium, smaller amounts of metals rather than larger amounts of metals incorporated into the zeolite/binder are preferred. Preferably the noble metals will range from the lower range of from about 5 ppm to upper range of about 2%, preferably about 1%, more preferably about 3000 ppm, most preferably about 2000 ppm by weight, basis metal, of the final catalyst. In a most preferred embodiment, it is preferred to use the noble metals in an amount sufficient to promote regeneration without deteriorating the performance of the catalyst, typically at about 30 ppm to about 100 ppm. Higher amounts of platinum and/or palladium, say, greater than about 2% by weight can have an adverse effect on the run life, olefin isomerization activity and/or selectivity of the catalyst.

The instant catalysts can be prepared by a variety of methods. In one embodiment, the zeolite is combined with the binder and formed into pellets by compaction or extrusion and the catalytic metal added by impregnation of the pellet with a metals-containing solution. After impregnation the catalyst is calcined at a temperature ranging from about 200° C. to about 700° C., preferably about 200° C. to about 650° C., more preferably about 300° C. to about 600° C.

In a preferred embodiment zeolite powder and alumina powder are mixed, say by mulling, with water and one or more compounds of the catalytic metal and the resulting mixture is formed into a pellet. It has been found that the catalysts prepared by mulling have superior olefin isomerization performance than the catalysts prepared by impregnation. The term "mulling" is used herein to mean mixing of powders to which sufficient water has been added to form a thick paste and wherein the mixing is accompanied by concomitant shearing of the paste. Commercially available mullers such as the Lancaster Mix Muller and the Simpson Mix Muller can be used to carry out the mulling.

Preferably the pellet is formed by extrusion. When extrusion is used, a peptizing acid(s), such as nitric acid, acetic acid, citric acid or mixtures thereof, is added to the mixture and optional extrusion aids such as cellulose derivatives, e.g., METHOCEL® F4M hydroxypropyl methylcellulose, are utilized (manufactured by The Dow Chemical Company). The amounts of peptizing acid used are readily determined by routine experimentation and will be an amount that provides a plastic, extrudable material. The term "pellets" as used herein can be in any shape or form as long as the materials are consolidated.

These pellets are calcined at a temperature ranging from a lower range of from about 200° C., preferably from about 300° C., more preferably from about 450° C., to an upper range of up to about 700° C., preferably up to about 600° C., more preferably up to about 525° C.

Hydrocarbon Feed Stream

The hydrocarbon feed useful for this invention comprises one or more linear alkenes. Typically, the linear alkene will contain four to ten carbon atoms. Also considered as linear alkenes for purposes of this invention are those alkenes containing a linear alkene segment with four to ten carbon atoms which can penetrate the zeolite catalyst for a distance effective to allow isomerization. Thus, the entire molecule need not be small enough to fit entirely within the pore structure of the catalyst. The preferred feed contains butylene and/or amylene.

As used herein, n-butylene includes all forms of n-butylene, for example 1-butene and 2-butene, either trans-2-butene or cis-2-butene, and mixtures thereof. As used herein, n-amylene or n-pentene, includes 1-pentene, cis- or trans-2-pentene, or mixtures thereof. The n-butylene or n-amylene used in the processes of this invention is generally in the presence of other substances such as other hydrocarbons. Thus, a feed stream used in the process of the invention containing n-butylene or n-amylene also can contain other hydrocarbons such as alkanes, other olefins, diolefins such as butadiene, aromatics, hydrogen, and inert gases. Typically, the n-butene feedstream used in this invention contains about 10 to about 100 wt. % n-butene. For example, a fractionated hydrocarbon feedstream from a fluid catalytic cracking effluent stream generally contains about 20 to about 60 wt. % normal butene and a hydrocarbon effluent from an ethers processing unit, such as methyl-tert-butyl ether (MTBE) generally contains from 40 to about 100 wt. % n-butylene- Feed streams from steam crackers and catalytic crackers may also contain substantial amounts of alkanes, say, up to about 80 wt. % . These feed streams may also be formed by selectively hydrogenating butadiene to form linear butenes.

As used herein, the term "alkene" can be alternatively referred to as "olefin"; the term "linear" can be alternatively referred to as "normal"; and the term "isoolefin" can be alternatively referred to as "methyl branched isoolefin." Similarly, butene and butylene refer to the same four carbon alkene; and pentene and amylene refer to the same five carbon alkene.

Isomerizing Conditions

In the processes of this invention, a hydrocarbon stream comprising at least one linear olefin is contacted with the catalytic zeolite under isomerizing conditions. Generally, in the processes of this invention, the hydrocarbon stream is contacted with the above-described zeolite catalyst in a vapor phase at a suitable reaction temperature, pressure and space velocity. Generally, suitable reaction conditions include a temperature of about 200° C. to about 650° C., preferably from about 340° C. to about 600° C., an olefin partial pressure of above about 0.5 atmosphere, and a total pressure of about 0.5 to about 10.0 atmospheres or higher, a hydrogen/hydrocarbon molar ratio of 0 to about 30 or higher, substantially free of water (i.e., less than about 2.0 wt % of the feed), and a hydrocarbon weight hourly space velocity (WHSV) of about 0.5 to about 100 $hr^{-1}$. These reactor streams can contain non-reactive diluents such as alkanes. The hydrogen can be added directly to the feed stream prior to introduction of the isomerization zone, or the hydrogen can be added directly to the isomerization zone.

The preferred reaction temperature will depend on a number of factors such as the pressure, the weight hourly space velocity and the feed composition, to name a few. Lower molecular weight olefins such as butenes are best isomerized at a temperature between about 200° C.–650° C. while higher molecular weight olefins are best isomerized at lower temperatures. Pentenes are best isomerized at a temperature between about 200° C.–550° C., and hexenes are best isomerized at a temperature between about 200° C.–500° C. Mixed butenes and pentenes are best isomerized at a temperature between about 200° C.–600° C. and mixed pentenes and hexenes are best isomerized at a temperature between about 200° C.–525° C. The use of a lower temperature may be advantageous when the olefin is easily cracked to lighter unwanted species at higher temperatures. It is also possible to achieve higher concentrations of desired products at lower temperatures due to the fact that higher equilibrium concentrations of the branched olefins are possible at lower temperatures.

In a typical butene isomerization process scheme, a butene vapor stream is contacted with such catalyst in a reactor at about 320° C. to about 650° C., at an olefin partial pressure of about 5 psia to about 50 psia and a total pressure of about 15 to about 100 psia and at an olefin based WHSV of about 0.5 to about 50 $hr^{-1}$. Preferred isomerizing conditions are carried out at a temperature of between about 320° C. to about 450° C., at atmospheric pressure, and an olefin based WHSV of between about 2 to about 25 $hr^{-1}$, more preferably between about 2 to about 15 $hr^{-1}$.

In a typical pentene isomerization process scheme, a pentene vapor stream is contacted with such catalyst in a reactor at about 250° C. to about 550° C., at an olefin partial pressure of about 3 psia to about 100 psia and a total pressure of about 15 to about 100 psia and at an olefin based WHSV of about 1 to about 100 $hr^{-1}$. Preferred isomerizing conditions are carried out at a temperature of between about 300° C. to 425° C., at atmospheric pressure, and an olefin based WHSV of between about 2 to about 40 $hr^{-1}$.

For a mixed feed, reaction conditions between pentene and butene isomerization processes can be used depending on the desired product mix.

The process of the present invention can utilize a combination of zeolites with one or more one dimensional pore structures having a pore size small enough to retard by-products dimerization and coke formation with the pore structure large enough to permit entry of the linear olefin(s) and diffusion of the isoolefin product(s). These combinations can include pellets of mixed zeolites and stacked bed arrangements of catalysts such as, for example, ZSM-22 and/or ZSM-23 over ferrierite, ferrierite over ZSM-22 and/or ZSM-23, and ZSM-22 over ZSM-23. The stacked catalysts can be of the same shape and/or size or of different shape and/or size such as ⅛ inch trilobes over 1/32 inch cylinders for example.

Regeneration Conditions

During the process, some coke will be formed on the surface of the catalyst. The surface of the catalyst where the coke builds up can be on the outer surface and/or on the surface of the inner channels and/or pores of the catalyst. Therefore, it is advantageous to regenerate the catalyst when at least 2%, preferably at least 5%, more preferably at least 10%, but before 30%, preferably before 25%, most preferably before 20 % by weight of coke build-up (basis uncoked catalyst).

When the build up of coke on the catalyst reaches a point where it needs to be regenerated, the hydrocarbon feed to the catalyst is stopped, any strippable hydrocarbon on the catalyst is stripped with hot gas (e.g. nitrogen and/or hydrogen) and the catalyst is then regenerated by subjecting it to heat treatment with an oxygen-containing gas. Stripping may be carried out at high pressure, under vacuum, or by cycling the reactor by pressurizing and depressurizing. Stripping may be combined with regeneration. For example, in a butene isomerization process, the butene feed can be stopped and replaced with hydrogen feed during stripping and then replaced with an oxygen-containing gas stream for regeneration.

The regeneration is preferably carried out at a temperature of at least 250° C. It is important that the temperature during regeneration remains less than about 565° C., preferably less than or equal to about 530° C., more preferably less than or equal to about 500° C., most preferably less than or equal to about 490° C. for a time effective to substantially burn off the coke on the surface of the coked catalyst. The coke is substantially burned off when more than about 80 % by weight of the coke is removed based on the initial total coke level when olefin isomerization or the linear olefin feed is stopped (hereinafter "weight % of the initial coke"). Preferably the regeneration is carried out until substantially all of the coke is burned off. Substantially all of the coke is burned off when more than about 95 weight % of the initial coke is removed. Regeneration temperatures are measured as average reactor environment temperatures (i.e., bulk gas phase temperatures) and occasional spikes for a short period of time or within a portion of the reactor environment is within the process of the invention. Coke as herein used is any oxidizable carbonaceous material. The coke levels can be conveniently measured by the coke test described below.

Preferable regeneration conditions include system pressures ranging from greater than 1 atmosphere, preferably from about 20 psig, to about 1500 psig, more preferably to about 1000 psig. The higher system pressure allows greater oxygen partial pressure while maintaining the ratio of oxygen to the inert gas used to absorb heat.

The oxygen partial pressure relative to total system pressure is typically within the range of from about 0.001 atmosphere, preferably from about 0.01 atmosphere, to about 40 atmospheres, preferably to about 10 atmosphere. Preferably the oxygen-containing gas is air, although the air may be diluted with additional nitrogen, carbon dioxide or hydrocarbon combustion products.

It is important in the regeneration process to avoid runaway exotherms above the desired maximum regeneration temperatures in the reactor. This can be accomplished by a suitable increasing of the temperature or by an increasing of the oxygen concentration in the oxygen-containing gas or both during the regeneration process in order to obtain a steady burn of the coke. Preferably the regeneration is carried out for a time sufficient to burn-off essentially all of the coke, say, down to a coke level of less than about 0.1 wt. % of the catalyst. Times will range from about 5 to about 200 hours, preferably from about 10 to about 100 hours. Preferably, no water is added during the regeneration process of the invention other than water present normally in air and/or regeneration gas used in the regeneration process.

The regeneration process of the invention allows for a smooth and controlled catalyst regeneration. The regeneration temperature can be sustained and controlled by regenerating the coke oxidation-promoting metal(s)-containing isomerization catalyst at elevated pressures.

The isomerization and/or regeneration process accordingly can be carried out in a packed bed reactor, a fixed bed, fluidized bed reactor or a moving bed reactor. The bed of the catalyst can move upward or downward. The isomerization process and the regeneration process may be carried out in the same bed or in separate beds. A continuous regeneration may be useful for the regeneration process. Regeneration may also be carried out ex situ.

In a preferred embodiment the invention can be defined as a process for structurally isomerizing a linear olefin of at least 4 carbon atoms to its corresponding methyl branched isoolefin which comprises:

(a) contacting at a temperature of from 200° C. to 650° C. a hydrocarbon feed stream containing at least one said linear olefin with an isomerizing catalyst comprising (i) at least one zeolite with one or more one-dimensional pore structure having a pore size small enough to retard by-product dimerization and coke formation with the pore structure and large enough to permit entry of the linear olefin and allow formation of the methyl branched isoolefin, (ii) a binder and (iii) a coke oxidation-promoting metal, (b) ceasing contact of the feed stream with the catalyst after coke build-up on the surface of the catalyst and optionally stripping any strippable hydrocarbon on the catalyst with hot gas, (c) contacting the thus-coked-catalyst with an oxygen-containing gas stream at a temperature of from about 250° C. to at most about 565° C. for a time effective to substantially burn off the coke based on the uncoked catalyst thereby regenerating the catalyst, and (d) repeating step (a) with the thus-regenerated catalyst.

In a preferred embodiment, steps (a) through (c) can be repeated at least 3 cycles, more preferably at least 10 cycles before the catalyst selectivity and/or isoolefin production decreases substantially. The isoolefin produced can be recovered or directly used in another process such as, for example, in a process to produce isoalkylethers as described in European Patent Publication Number 523,838 and U.S. Pat. No. 5,191,146.

For this process, the catalyst utilized is preferably prepared by the process comprising:

(1) mixing by mulling together zeolite powder, alumina powder, water, peptizing amount of acid and a compound of the coke oxidation-promoting metal, (2) forming a pellet of the mixture of (1), and (3) calcining the pellet of (2) at a temperature of from 300° C. to 700° C.

The invention further relates to the unique catalysts prepared as described herein, particularly where those catalysts are prepared by mulling.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The following illustrative embodiments are provided to illustrate the invention and are not intended to be construed to limiting the inventions to such embodiments.

Preparation of the Catalyst

The following examples illustrate methods of preparation of catalysts useful for isomerizing olefins to isoolefins. Two ammonium ferrierite powders, ZSM-22 and ZSM-23 powders were used to prepare the catalysts used in the examples described below. The two ammonium ferrierites were prepared in an identical fashion and exhibited similar physical and catalytic properties. Catalysts A, C, E and F were prepared using ammonium-ferrierite with a molar silica to alumina ratio of 53:1, a surface area of 391 m2/g (P/Po= 0.03), a soda content of 292 ppm wt and a n-hexane sorption capacity of 7.2 grams per 100 grams of zeolite. Catalyst B, B' and D were made using ammonium-ferrierite having a molar silica to alumina ratio of 62:1, a surface area of 369 m2/g (P/Po=0.03), a soda content of 480 ppm wt and a n-hexane sorption capacity of 7.3 grams per 100 grams of zeolite. Catalyst H was prepared using ZSM-22 (also known as Theta-1 and TON) prepared according to the procedures in Example TON-C in European Patent Application No. 247,802. Catalyst I was prepared using ZSM-23 prepared according to the procedures in Example ZSM-23 in European Patent Application No. 247,802.

The catalyst components were mulled using a Lancaster mix muller. The mulled catalyst material was extruded using a Bonnot pin barrel extruder.

The binder utilized was CATAPAL® D alumina from Vista Chemical Company and METHOCEL®(R) F4M hydroxypropyl methylcellulose from The Dow Chemical Company was used as an extrusion aid.

Catalyst A—No Palladium

The Lancaster mix muller was loaded with 944 grams of ammonium-ferrierite (34.2% loss on ignition ("LOI") determined at a temperature of 900° C.) and 93 grams of CATAPAL® D alumina (LOI of 25.8%). The alumina were blended with the ferrierite for 5 minutes during which time 78 milliliters of de-ionized water were added. A mixture of 8 grams glacial acetic acid and 78 milliliters of de-ionized water were added slowly to the muller in order to peptize the alumina. Ten grams of METHOCEL® (R) F4M hydroxypropyl methylcellulose were added and the zeolite/alumina mixture was mulled for 15 additional minutes. The extrusion mix had an LOI of 42.5%. The 90:10 zeolite/alumina mixture was transferred to the Bonnot extruder and extruded using a stainless steel die plate with 1/16' holes. The extrudate was dried at 120° C. for 16 hours and then calcined in air at 500° C. for 2 hours.

Catalyst B—100 ppm Palladium by Mulling

The Lancaster mix muller was loaded with 632 grams of ammonium ferrierite (LOI of 3.4%) and 92 grams of CATAPAL®D alumina (LOI of 26.2%). The alumina was blended with the ferrierite for five minutes during which time 156 milliliters of de-ionized water were added. A mixture of 6.8 grams of glacial acetic acid and 156 milliliters of de-ionized water were added slowly to the muller in order to peptize the alumina. The mixture was mix-mulled for 10 minutes. 0.20 Grams of tetraammine palladium nitrate in 156 milliliters of de-ionized water were then added slowly as the mixture was mulled for a period of 5 additional minutes. Ten grams of Methocel® F4M hydroxypropyl methylcellulose was added and the zeolite/alumina was mulled for 15 additional minutes. The extrusion mix had a LOI of 43.5%. The 90:10 extrudate was transferred to a Bonnot pin barrel extruder and extruded using a stainless steel die plate with 1/16 inch holes. The extrudate was dried at 120° C. for 16 hours and then calcined in air at 500° C. for 2 hours.

Catalyst B'—100 ppm Palladium by Mulling

The Lancaster mix muller was loaded with 645 grams of ammonium-ferrierite (5.4% LOI) and 91 grams of CATAPAL® D alumina (LOI of 25.7%). The alumina was blended with the ferrierite for 5 minutes during which time 152 milliliters of de-ionized water were added. A mixture of 6.8 grams glacial acetic acid, 7.0 grams of citric acid and 152 milliliters of de-ionized water were added slowly to the muller in order to peptize the alumina. The mixture was mulled for 10 minutes. 0.20 Grams of tetraamine palladium nitrate in 153 grams of deionized water were then added slowly as the mixture was mulled for a period of 5 additional minutes. Ten grams of METHOCEL®(R) F4M hydroxypropyl methylcellulose were added and the zeolite/alumina mixture was mulled for 15 additional minutes. The extrusion mix had an LOI of 43.5%. The 90:10 zeolite/alumina mixture was transferred to the Bonnot extruder and extruded using a stainless steel die plate with 1/16" holes. The extrudate was dried at 120° C. for 16 hours and then calcined in air at 500° C. for 2 hours.

Catalyst C—30 ppm Palladium by Mulling

The method used to prepare Catalyst B was used, with appropriate adjustment of ingredient concentrations, to prepare a catalyst having 30 ppm by weight of palladium.

Catalyst D—2500 ppm Palladium by Mulling

The method used to prepare Catalyst B was used, with appropriate adjustment of ingredient concentrations, to prepare a catalyst having 2500 ppm by weight of palladium.

Catalyst E—100 ppm Palladium by Impregnation

Catalyst E was prepared by pore volume impregnation of Catalyst A. 15 Grams of Catalyst A were impregnated with a solution containing:

1) 0.015 grams of a palladium nitrate aqueous solution containing 10% wt of palladium and
2) 9.6 grams of absolute ethyl alcohol.

The contact was maintained for one hour at room temperature. Then the mixture was dried at 120° C. for 16 hours and calcined in air at 500° C. for 2 hours.

Catalyst F 100 ppm Palladium by Impregnation

Catalyst F was prepared in a manner similar to Catalyst E except 0.0043 grams of Bis(acetylacetonato) palladium was dissolved in 9.6 grams of absolute ethyl alcohol.

Catalyst G—1000 ppm Palladium by Mulling

The method used to prepare Catalyst B was used, with appropriate adjustment of ingredient concentrations, to prepare a catalyst having 1000 ppm by weight of palladium.

Catalyst H—100 ppm Palladium by Mulling

The method used to prepare Catalyst B was used except ZSM-22 was used instead of ammonium ferrierite to prepare a catalyst having 100 ppm by weight of palladium by mulling. The zeolite/alumina mixture was extruded using a Bonnot extruder equipped with a stainless steel die plate with 1/16 inch holes. The extrudate was dried at 120° C. for 16 hours and then calcined in air at 500° C. for 2 hours.

Catalyst I—100 ppm Palladium by Mulling

The method used to prepare Catalyst B was used except ZSM-23 was used instead of ammonium ferrierite to prepare a catalyst having 100 ppm by weight of palladium by mulling. The zeolite/alumina mixture was extruded using a Bonnot extruder equipped with a stainless steel die plate with 1/16 inch holes. The extrudate was dried at 120° C. for 16 hours and then calcined in air at 500° C. for 2 hours.

Testing Procedure

Coke Test

In an analytical test, the weight of coke on the catalyst is determined by measuring the amount of weight lost after complete combustion of the coke in an oxygen containing stream at an elevated temperature, typically at 750° C. for one hour. Care should be taken to minimize uptake of water by the catalyst.

Isomerization I

A stainless steel tube, 1 inch OD, 0.6 inch ID and 26 inches long was used as a reactor. A thermowell extended 20 inches from the top of the tube. To load the reactor, it was first inverted and a small plug of glass wool was slid down the reactor tube over the thermowell until it hit the bottom of the tube. Silicon carbide (20 mesh) was added to a depth of about 6 inches. Over this was placed a small plug of glass wool. Approximately 4 grams of catalyst particles, 6–20 mesh, admixed with about 60 grams of fresh silicon carbide (60–80 mesh) were added in two parts to distribute the catalyst evenly. The catalyst bed was typically about 10 inches long. Another piece of glass wool was added to the top of the catalyst and the reactor was topped with 20 mesh silicon carbide, followed by a final plug of glass wool. A multipoint thermocouple was inserted into the thermowell and was positioned such that the temperature above, below and at three different places in the catalyst bed could be monitored. The reactor was inverted and installed the furnace.

The feed utilized was 1-butene obtained from Scott Specialty Gases with a 1-butene content of greater than 99.2% weight. The 1-butene was fed to the reactor in the gas phase.

To start up the reactor, it was first heated to the desired operating temperature over a four hour period and held at the operating temperature for 2 hours, all under flowing nitrogen. After this pretreatment, the nitrogen flow was shut off and the 1-butene was added at a rate of 36 g/hr to give the desired weight hourly space velocity of 9.0 hr$^{-1}$. The reactor was operated at an outlet pressure of 3 psig and at a temperature of 430° C.

Regeneration I

After running the catalysts in the isomerization process described above, they were found to be black due to the build-up of carbonaceous material (coke) comprising about 10 to 20% wt. Each catalyst was removed from the test reactor and its weight was measured. The catalysts were each reloaded into a test reactor and regenerated by the following procedure. The unit was pressurized to 90 psig and a flow of approximately 6 standard liters per hour of air was started. The sample was heated by the following controlled heating procedure: ramp from 25° C. to 125° C. at 10° C. per minute; hold at 125° C. for 30 minutes; ramp from 125° C. to 350° C. at 2° C. per minute; ramp from 350° C. to 470° C. at 1° C. per minute and hold at 470° C. for 24 hours. The reactor was then cooled and the catalyst unloaded. Substantially complete regeneration of the catalyst was confirmed by the disappearance of the black color of the unregenerated catalyst. Samples of the catalysts were weighed to measure coke loss.

Isomerization II

A flanged, stainless steel pipe, 2.88 inch OD, 2.5 inch ID and 17 feet long was used as a reactor. A second flanged, stainless steel pipe, 2.38 inch OD, 2 inches ID and 12 feet long was used as the feed preheater. The preheater was positioned next to the reactor and was connected by a three foot U-bend at the top. A thermowell, containing ten thermocouples ranging in length from 30 inches to 80 inches, was attached to the bottom flange and runs up into the reactor. Electrical heating elements span the length of the reactor and preheater. The preheater was loaded with 1/4 inch support balls to a level of four feet measured from the top. The reactor was first loaded with 1/4 inch support balls to a level of 15 feet from the top of the reactor. Next, six inches of 1/8 inch support balls were added. 3.43 Pounds of catalysts was then poured into the reactor directly on top of the 1/8 inch support balls.

The feed utilized was a commercial grade raffinate-2 containing approximately 40 wt. % 1-butene, 20 wt. % trans-2-butene, 13 wt. % cis-2-butene, 3 wt. % isobutane, 23 wt. % n-butane and 1 wt. % isobutylene. The raffinate-2 was fed to the preheater in the gas phase following vaporization in a low pressure steam preheater.

At start up, the reactor was heated to 288° C. under flowing nitrogen. After a period of four hours, the gas exiting the reactor was sampled for oxygen content. Once the oxygen content dropped below 0.02 vol. %, the pretreatment step was complete and nitrogen flow was discontinued. This step took approximately 9 hours. The raffinate-2 was added to the reactor at a rate of 24 lbs/hr to give a desired weight hourly space velocity of 7.0 hr$^{-1}$. As soon as raffinate-2 feed was introduced to the reactor, the temperature was increased to the desired operating temperature. The isomerization reaction was continued until an average of 35% normal olefin conversion was reached.

Regeneration II

The reactor outlet was lined up to a flare header. The feed was blocked and nitrogen was introduced to the reactor and the bed temperature was cooled to 343° C. Nitrogen flow was slowly increased to a maximum of 350 standard cubic feet per hour ("SCFH") at atmospheric pressure for several hours until the effluent purge gas was hydrocarbon free while maintaining a uniform catalyst bed temperature of 343° C. Dry air was introduced to the reactor at 13.6 SCFH while maintaining the nitrogen flow rate of 350 SCFH. The burn was monitored by observing any temperature increase across the catalyst bed once the mixed gas was introduced to the reactor. The catalyst bed temperature was maintained so as not to exceed 471° C. Once the oxygen content (both oxygen and carbon dioxide) reached 1.75 mol %, temperature was recorded across the catalyst bed. The temperature was maintained at 471° C.

Once the carbon dioxide produced fell below 0.05 mol %, the temperature was slowly increased at a rate of 3–6° C. per hour up to a temperature of 485° C. using an electric heater. As the bed temperature began to drop, air flow rate to the reactor was slowly increased in 5–10 SCFH increments to reach a maximum bed temperature of 487° C. Air flow of up to the maximum of 205 SCFH was continued while maintaining the bed temperatures at 487° C. until the bed temperatures started to fall at which time nitrogen flow was slowly removed from the system. The regeneration was continued in pure air at the 205 SCFH air rate for 12 hours while maintaining the bed temperature at 487° C. The regeneration was further continued until less than 0.01 mol % of carbon dioxide was present in the flue gas for one hour. Then the reactor was cooled to a temperature of 288° C. and purged with nitrogen.

Isomerization III

The reactor was a 2 inch OD and 1.6 inch ID stainless steel pipe with 2-inch flanges welded to each end. The pipe also had ¼ inch feed and effluent lines welded on 6 inches from the bottom and top of the reactor, respectively. The top sealing flange was fitted with a pressure gauge and rupture disk. The bottom sealing flange was fitted with a thermwell welded directly in the center of the flange that was extended up through the middle of the reactor pipe when attached. The thermowell was a stainless steel tube welded shut at one end and contained eight or more thermocouple points. The reactor pipe was enclosed with a Lindberg three foot heating furnace containing three heating zones but only the bottom zone was used to preheat the butylene feed to the reaction section. The furnace was controlled by three controllers. Located on the effluent line was tubing and equipment for sampling the hydrocarbon effluent directly to a gas chromatograph.

The feed utilized was an MTBE processing effluent and contained approximately 25–35 weight percent butene-2, 40–50 weight percent butene-1, and 20–30 weight percent butanes.

The reactor was first loaded with an inert packing material in the preheating zone. The inert packing materials used were either a small mesh corundum or inert clay catalyst support balls. Above the packing material a preweighed amount of catalyst was added to form a distinct zone of catalyst.

At start up, the reactor was heated to a minimum operating temperature usually greater than 200° C. under flowing nitrogen purge at approximately 15–50 psia. Once the reactor was heated, the feed was introduced to the reactor and the nitrogen purge was stopped. The isomerization reaction was carried out at a WHSV of 7 hr$^{-1}$ and at a temperature of 430° C.

Regeneration III

A muffle furnace was preheated to 500° C. The coked catalyst was separated from the catalyst support balls. The catalyst was placed evenly in a stainless steel pan with approximate dimensions of 12 inches by 6 inches. The metal pan with the catalyst was placed into the preheated muffle furnace. Once the catalyst reached a white or near white appearance, the metal pan was removed from the muffle furnace. The catalyst was transferred to a beaker and allowed to cool in a desiccator to room temperature.

Calculations

Conversion and selectivity were calculated for each sample during testing runs and used for comparison of the various catalysts. The calculation of conversion and selectivity reflect the feed (FD) and effluent (EFF) concentrations of butene-1 (B1) and butene-2 (B2) and isobutylene (IB1). Conversion is calculated as:

$$\% \text{ Conversion} = \frac{(wt\% B1 + wt\% B2)FD - (wt\% B1 + wt\% B2)EFF}{(wt\% B1 + wt\% B2)FD} \times 100$$

selectivity is calculated as:

$$\% \text{ Selectivity} = \frac{(wt\% IB1)EFF - (wt\% IB1)FD}{(wt\% B1 + wt\% B2)FD - (wt\% B1 + wt\% B2)EFF} \times 100$$

and yield is calculated as $$\% \text{ Yield} = \frac{(wt\% IB1)EFF - (wt\% IB1)FD}{(wt\% B1 + wt\% B2)FD} \times 100$$

EXAMPLES 1–9

Table 1 shows the results of the testing of the various catalysts prepared above. This Table provides the hours of run life of the catalyst in the isomerization process after various regeneration cycles. Butene was isomerized according to Isomerization I and the catalyst was regenerated according to Regeneration I for Table 1. "Run life" (in hours) is defined herein as the time from start-of-run to the time at which the concentration of methyl branched isoolefin in the product has declined to 27 wt. % after having reached its peak. The Table also provides the instantaneous selectivities to isobutylene of the catalysts at 40% conversion, 45% conversion, and 50% conversion and the highest concentration (% wt) of the methyl-branched isoolefin (isobutylene) in the product achieved during testing. Examples 1–9 are listed from top to bottom in Table 1.

TABLE I

| CATALYST | PD (ppm) | REGEN. No[a] | METHOD OF PD ADDITION | % SELECT. AT A FIXED CONV. 50% CONV. | 45% CONV. | 40% CONV. | RUN LIFE, HOURS | MAX IB PROD. DURING RUN |
|---|---|---|---|---|---|---|---|---|
| A | 0 | 0 | None Added | 69 | 77 | 81 | 155 | 34.6 |
|   | 0 | 1 | None Added | 63 | 72 | 76 | 110 | 31.7 |
|   | 0 | 2 | None Added | 59 | 69 | 73 | 84 | 30.1 |
|   | 0 | 3[b] | None Added | 36 | — | — | [d] | 20.6 |
| C | 30 | 0 | Co-mulled | 67 | 73 | 78 | 142 | 33.3 |
|   | 30 | 1[b] | Co-mulled | 53 | 60 | 64 | 35 | 27.5 |
|   | 30 | 2[c] | Co-mulled | 57 | 64 | 69 | 90 | 29.4 |
| B | 100 | 0 | Co-mulled | 69 | 78 | 83 | 135 | 35.2 |
|   | 100 | 1 | Co-mulled | 69 | 79 | 84 | 165 | 35.4 |
|   | 100 | 2 | Co-mulled | 69 | 77 | 82 | 171 | 34.5 |
|   | 100 | 3 | Co-mulled | 70 | 78 | — | [g] | 35.2 |
|   | 100 | 4 | Co-mulled | 69 | 78 | 83 | 142 | 35.3 |
| B' | 100 | 0 | Co-mulled | 74 | 83 | 88 | 317 | 38.2 |
|   | 100 | 1 | Co-mulled | 73 | 83 | 88 | 214[e] | 37.4 |
|   | 100 | 2 | Co-mulled | 74 | 83 | 88 | 284 | 38.2 |
|   | 100 | 3 | Co-mulled | 71 | 81 | — | 160[f] | 36.5 |
|   | 100 | 4 | Co-mulled | 72 | 81 | 87 | 283 | 36.2 |
| D | 2500 | 0 | Co-mulled | 63 | 72 | 80 | 129 | 32.6 |
| E | 100 | 0 | Impregnation | 64 | 72 | 80 | 115 | 32.6 |
|   | 100 | 1 | Impregnation | 62 | 71 | 77 | 126 | 32.1 |
| F | 100 | 0 | Impregnation | 63 | 70 | 79 | 102 | 32.6 |
| G | 1000 | 0 | Co-mulled | 64 | 73 | 81 | 135 | 32.9 |
| H | 100 | 0 | Co-mulled | 44 | — | — | [h] | 25.1 |
|   | 100 | 1 | Co-mulled | 44 | — | — | [i] | 24.8 |

[a] Except as otherwise noted, regeneration was carried out at 470° C. in 90 psig air at a gaseous hourly space velocity of 700 $h^{-1}$ for a period of 24 hours.
[b] 500° C., 90 hrs, 1 ATM in muffle furnace
[c] 490° C., 24 hrs, 3 ATM (30 psig)
[d] Did not ever achieve 27% IB in product; maximum was only 20.6%.
[e] Terminated run before 27% IB in product was obtained (terminated at 32.5%).
[f] Terminated run before 27% IB in product was reached (terminated at 34.5%).
[g] Terminated run before 27% IB in product was reached (terminated at 34.9%).
[h] Terminated run before 27% IB in product was reached; maximum was only 25.1%.
[i] Terminated run before 27% IB in product was reached; maximum was only 24.8%.

As can be seen from Table 1, catalysts containing palladium (see Catalyst B) gave longer run life and/or achieved higher selectivities to isobutylene over a number of regenerations whereas catalysts without palladium (see Catalyst A) showed substantial decline in catalyst run life and/or selectivity. For Catalyst B, catalyst run life remained above 130 hours over 4 regenerations whereas for Catalyst A run life dropped below 100 run hours within 2 regenerations. The time required for regeneration was much less than the run lives for the catalysts of the present invention. Further, the selectivity of the catalysts with palladium remained substantially the same with minimal decline (0–2% change for Catalysts B, B', E, and H) whereas the selectivity of the catalysts without palladium declined significantly every regeneration (3–5% decline for catalyst A).

Regenerations at higher temperatures, atmospheric pressure and without palladium resulted in a loss in the catalyst selectivity at fixed conversions. This loss became more pronounced with repeated regenerations.

Further, as can be seen from Table 1, the catalysts in which palladium has been incorporated by mulling demonstrate increased run life, higher isobutylene yield and higher selectivities at 40% conversion, 45 % conconversion and 50% conversion levels when compared to catalyst(s) prepared by impregnation. The long cycle life and high selectivities of the palladium co-mulled catalysts were maintained after multiple regenerations at elevated pressure and lower temperatures.

The selectivity of 2500 ppm palladium-incorporated Catalyst D is lower than the selectivity of 100 ppm palladium-incorporated Catalyst B. High levels of oxidation-promoting metal(s) incorporated in the catalysts, above 15% by weight, basis metal, of the total weight of the catalyst results in unacceptably reduced selectivity and/or run length. In the preferred embodiment, palladium is used in a sufficient amount to assist with the regeneration but less than an amount which will severely limit the run life of the catalyst.

EXAMPLES 10–14

Table 2 shows the times (at maximum temperature) required for coke removal from Catalysts A and B at various temperatures and pressures. This data was generated using pressure thermogravimetric analysis.

TABLE 2

| EXAMPLES | CATALYST | PRESSURE, ATM | MAX TEMP. | TIME, HR* | Pd, PPM |
|---|---|---|---|---|---|
| 10 | A | 1 | 500 | 90 | — |
| 11 | A | 1 | 530 | 12 | — |
| 12 | B | 1 | 530 | 6 | 100 |
| 13 | A | 8 | 470 | 14 | — |

TABLE 2-continued

| EXAMPLES | CATALYST | PRESSURE, ATM | MAX TEMP. | TIME, HR* | Pd, PPM |
|---|---|---|---|---|---|
| 14 | B | 8 | 470 | 9 | 100 |

*At maximum temperature, time represents the time at which no weight lost is observed under the same conditions using pressure thermogravimetric analysis.

The use of palladium and/or higher oxygen partial pressures allows the coke on the catalyst to be removed in shorter periods of time and at lower temperatures. As can be seen from Table 2, catalysts incorporating palladium (Examples 12 and 14) were able to regenerate at reduced time compared with catalysts with no palladium (Examples 11 and 13). Further, the palladium-containing catalyst in Example 14 which was regenerated at a pressure of 8 atmosphere (and elevated oxygen partial pressure) regenerated faster at lower temperature compared to Examples 10 and 11. As can be seen by Examples 13 and 14, elevated pressure allows catalysts to be regenerated at lower temperatures within a shorter time.

EXAMPLE 15

Catalyst A (no palladium) was used to isomerize a butene feed stock under Isomerization III and Regeneration III conditions. The average selectivity to isobutene over a number of regenerations is plotted in FIG. 1. Catalyst B (with palladium) was used to isomerize a butene feed stock under Isomerization II and Regeneration II conditions. The average selectivity to isobutene over a number of regenerations is plotted in FIG. 1 for this catalyst. The line for Catalyst B represents a linear regression of 19 data points.

As can be seen from FIG. 1, the high selectivity of Catalyst B can be maintained through at least 19 regenerations by using the process of the present invention.

All of the data presented in Table 1 were obtained using a commercially available butene feed with a purity of 99.2% or greater. The data shown in FIG. 1 were obtained using a feed stream containing 70–75% butenes and 25–30% butanes. These differences in the feeds result in higher selectivities for butane-containing feeds as can be seen in FIG. 1. The presence of butanes (or other diluents such as nitrogen) in the olefinic stream serves to lower the olefin partial pressure which leads to a reduction in the amount of non-$C_4$ products produced. Similar increases in selectivities have been reported when the olefin content has been diluted with less reactive gases such as nitrogen as seen in Table 7 of European Application No. 247,802. It is useful to note that with the ferrierite based catalysts such as Catalyst B' very high selectivities can be obtained with both diluted and undiluted olefinic streams.

We claim:

1. A process for structurally isomerizing a linear olefin of at least 4 carbon atoms to its corresponding methyl branched isoolefin which comprises:

(a) contacting at a temperature of from 200° C. to 650° C. a hydrocarbon feed stream containing at least one said linear olefin with an isomerizing catalyst comprising (i) a hydrogen form of a zeolite having a ferrierite isotypic framework structure, ZSM-22 or ZSM-23, (ii) a binder and (iii) a coke oxidation-promoting metal, (b) ceasing contact of the feed stream with the catalyst after coke build-up on the surface of the catalyst, (c) contacting the catalyst from step (b) with an oxygen-containing gas at a temperature of no more than 490° C. a system pressure of greater than 1 atmosphere, and an oxygen partial pressure of from about 0.001 atmosphere to about 40 atmospheres to burn off coke from the catalyst and (d) repeating steps (a) with the catalyst from step (c).

2. The process of claim 1 wherein the coke oxidation-promoting metal compound is present in an amount sufficient to provide in the final catalyst from about 5 ppm to about 15% by weight of the metal.

3. The process of claim 2 wherein step (c) is carried out for a time within the range from about 5 to 200 hours.

4. The process of claim 3 wherein the coke oxidation-promoting metal is a metal selected from Groups IB, VB, VIB, VIIB and VIII of the Periodic Table of Elements.

5. The process of claim 4 wherein the coke oxidation-promoting metal compound is present in an amount sufficient to provide in the final catalyst from about 5 ppm to about 10% by weight of the metal.

6. The process of claim 5 wherein the coke oxidation-promoting metal is a metal selected from Pd, Pt, Ni, Co, Mn, Ag, Cr and mixtures thereof.

7. The process of claim 5 wherein the coke oxidation-promoting metal is a noble metal.

8. The process of claim 7 wherein the coke oxidation-promoting metal is selected from palladium, platinum and mixtures thereof.

9. The process of claim 8 wherein the coke oxidation-promoting metal compound is present in an amount sufficient to provide in the final catalyst from about 5 ppm to about 3000 ppm by weight of the metal.

10. The process of claim 9 wherein the coke oxidation-promoting metal compound is present in an amount sufficient to provide in the final catalyst from about 5 ppm to about 2000 ppm by weight of the metal.

11. The process of claim 10 wherein step (b) is carried out after coke build-up is at least 2% by weight based on uncoked catalyst.

12. The process of claim 3 wherein step (b) is carried out after coke build-up is at least 2% by weight based on uncoked catalyst.

13. The process of claim 1 wherein zeolite and binder is present in an amount sufficient to provide in the final catalyst from 60 to 99.5 percent by weight of zeolite and from 0.5 to 40 percent by weight of binder.

14. The process of claim 13 wherein zeolite and binder is present in an amount sufficient to provide in the final catalyst from 80 to 98 percent by weight of zeolite and from 2 to 20 percent by weight of binder and the coke-oxidation metal is a noble metal.

15. The process of claim 1 wherein the binder is selected from natural clays, titania, zirconia and mixtures thereof.

16. The process of claim 15 wherein the natural clays are selected from attapulgite, bentonite, kaolin, montmorillonite and mixtures thereof.

17. The process of claim 1 wherein the binder is selected from alumina, silica-alumina and clay.

18. The process of claim 17 wherein the binder is alumina.

19. The process of claim 1 wherein the zeolite is a hydrogen form of a zeolite having a ferrierite isotypic framework structure.

20. The process of claim 19 wherein the zeolite is selected from the group consisting of Sr-D, FU-9, ISI-6, ferrierite, NU-23, ZSM-35, ZSM-38 and mixtures thereof.

21. The process of claim 1 wherein the zeolite is selected from the group consisting of ZSM-22 and ZSM-23.

22. The process of claim 1 wherein the hydrocarbon feed steam comprises a linear alkene having four to ten carbon atoms.

23. The process of claim 22 wherein the hydrocarbon feed stream comprises n-butylene and/or n-amylene.

24. The process of claim 1 wherein the catalyst is prepared by the process comprising:
   (1) mulling together zeolite powder, alumina-containing binder, water, peptizing amount of acid and a compound of the coke oxidation-promoting metal,
   (2) forming a pellet of the mixture of (1), and
   (3) calcining the pellet of (2) at a temperature of from 200° C. to 700° C.

25. A process for structurally isomerizing a linear olefin of at least 4 carbon atoms to its corresponding methyl branched isoolefin which comprises:
   (a) contacting at a temperature of from 200° C. to 650° C. a hydrocarbon feed stream containing at least one said linear olefin having four to ten carbon atoms with an isomerizing catalyst comprising (i) ferrierite, (ii) an alumina binder wherein the weight ratio in the finished catalyst of ferrierite to alumina ranges from about 60:40 to about 99.5:0.5, and (iii) from about 5 ppm to about 5% by weight of palladium and/or platinum,
   (b) ceasing contact of the feed stream with the catalyst after coke build-up of at least 2% by weight based on uncoked catalyst,
   (c) contacting the thus-coked catalyst with an oxygen-containing gas stream at a temperature of from 250° C. to no more than 490° C. thereby burning off coke from the catalyst, and
   (d) repeating step (a) with the catalyst from step (c).

26. The process of claim 25 wherein the catalyst is prepared by the process comprising:
   (1) mixing by mulling together ferrierite powder, alumina, water, a peptizing amount of acid and a palladium and/or a platinum compound,
   (2) forming a pellet of the mixture of (1), and
   (3) calcining the pellet of (2) at a temperature of from 200° C. to 700° C.

27. The process of claim 26 wherein the weight ratio of ferrierite to alumina ranges from about 85:15 to about 95:5, the amount of palladium and/or platinum ranges from about 5 ppm to about 1000 ppm by weight, the temperature of step (c) ranges from about 400° C. to no more than 490° C., and the calcining temperature in step (3) ranges from about 450° C. to about 525° C.

* * * * *